(12) United States Patent
Murata et al.

(10) Patent No.: US 8,496,949 B2
(45) Date of Patent: Jul. 30, 2013

(54) POWDER COSMETIC AND PROCESS FOR PRODUCTION OF FLAKY CALCIUM SULFATE DIHYDRATE TO BE USED IN THE COSMETIC

(75) Inventors: Togo Murata, Chiyoda-ku (JP); Tetsuo Murata, Chiyoda-ku (JP)

(73) Assignee: Ohken Co. Ltd., Chiyoda-Ku, Tokyo (JP)

( * ) Notice: Subject to any disclaimer, the term of this patent is extended or adjusted under 35 U.S.C. 154(b) by 525 days.

(21) Appl. No.: 12/678,615

(22) PCT Filed: May 30, 2008

(86) PCT No.: PCT/JP2008/060033
§ 371 (c)(1),
(2), (4) Date: Mar. 17, 2010

(87) PCT Pub. No.: WO2009/037901
PCT Pub. Date: Mar. 26, 2009

(65) Prior Publication Data
US 2010/0202990 A1  Aug. 12, 2010

(30) Foreign Application Priority Data

Sep. 19, 2007 (JP) .................................. 2007-241820
Dec. 13, 2007 (JP) .................................. 2007-321491

(51) Int. Cl.
*A61K 8/02* (2006.01)
(52) U.S. Cl.
USPC ......................................... 424/401; 424/489

(58) Field of Classification Search
None
See application file for complete search history.

(56) References Cited

U.S. PATENT DOCUMENTS

| 5,885,342 | A * | 3/1999 | Gale et al. ..................... 106/417 |
| 6,235,295 | B1 * | 5/2001 | Bodelin-Lecomte et al. 424/401 |
| 2001/0007677 | A1 * | 7/2001 | Nagatani et al. .............. 424/401 |

FOREIGN PATENT DOCUMENTS

| JP | 2003246711 A | 2/2003 |
| JP | 2005220057 A | 8/2005 |
| JP | 2005289975 A | 10/2005 |

* cited by examiner

*Primary Examiner* — Anand Desai
*Assistant Examiner* — Melissa Mercier
(74) *Attorney, Agent, or Firm* — Browdy and Neimark, PLLC (57) ABSTRACT

The invention aims at providing a powder cosmetic which does not suffer from the aggregation of powder even when it contains a large amount of oily component and in which no caking of powder on the surface occurs even when pressed, and a process for the production of platy calcium sulfate dihydrate usable for the cosmetic. The process of the production includes a process for producing a powder cosmetic comprising calcium sulfate dihydrate and an oily component, and a process for producing platy calcium sulfate dihydrate which process comprises dissolving a calcium salt in an organic acid and reacting the resulting calcium solution with sulfuric acid.

13 Claims, 1 Drawing Sheet

POWDER COSMETIC AND PROCESS FOR PRODUCTION OF FLAKY CALCIUM SULFATE DIHYDRATE TO BE USED IN THE COSMETIC

TECHNICAL FIELD

The present invention relates to powder cosmetics into which a larger amount of oily component than in the conventional powder cosmetics can be blended, and a process for producing platy calcium sulfate dihydrate to be used in the cosmetics.

BACKGROUND ART

Powder cosmetics containing powder components, such as powder foundation and eye shadow, are placed in a major category in the field of cosmetics.

These powder cosmetics can be produced by dispersing an extender, pigment, and the like, homogeneously into an oily component as binder to give a powder mixture, and molding the mixture placed on a metal plate by press packing.

Among the powder components used in the above-mentioned powder cosmetics, naturally occurring thin sheet-like mica flake, sericite, talc, and the like, or their surface-processed products have been employed as an extender because they are excellent in extensibility and adhesiveness to the skin. In addition, organic powder including really spherical nylon powder has been used together with the above extender to improve the smoothness or touch of the extender on the skin. Further, white pigment such as titanium dioxide, coloring pigment such as iron oxide red, and pearlescent pigment such as mica titanium, have been used as pigments.

When the above powder components are used in these powder cosmetics, the total amount of the oily components blended into the powder cosmetics has been limited approximately to the range of 15 mass % or less, though a little difference is recognized depending on the kind of powder component. The reason is that the excessive amount of the oily component over the above-mentioned range yields aggregation in the powder to give a product far from a powder cosmetic, and further it forms caking on the surface of fillers (a phenomenon that the surface becomes so hard as to make its removal with a powder puff difficult), causing a problem to make the use as powder cosmetic difficult, though there is a favorable tendency to increase a wet sense and fitting to the skin with increase of the amount of the oily component.

As an extender for the powder cosmetics, gypsum (calcium sulfate dihydrate), the same type of natural mineral as conventionally-used mica flake, sericite, talc, and the like, may be used. The gypsum itself, however, had not yet been utilized as an extender for powder cosmetics, though calcined gypsum (half-hydrate of gypsum) has been used as a cosmetic pack and the like utilizing its property to solidify through chemical reaction with water.

The gypsum, in addition to natural gypsum, includes chemically synthesized chemical gypsum, which can be produced in various ways and generated in diverse crystal forms depending on the condition of the production. For example, the chemical gypsum is known in the forms of fiber, rice grains, globules, relatively-thick plates and the like (Patent documents 1-15). There is, however, a problem of complexity and much danger involved in the chemicals and the reaction conditions to be employed in the processes for producing these chemical gypsums.

Recently, a process for producing chemical gypsum in a platy form was published (Patent document 16). In this process, a heated solution of gypsum is allowed to stand under cooling until the supersaturation reaches 0.15 mol/L or more and then crystallized out rapidly with stirring to produce the chemical gypsum in a platy form.

This process is, however, expensive and dangerous because it is necessary to heat the mixture at a temperature higher than or equal to 80° C. and lower than 100° C. during dissolving and then using a strong corrosive mineral acid such as hydrochloric acid and nitric acid at such a high temperature.

Patent document 1: JP 2002/29740A
Patent document 2: JP 7/330329A (1995)
Patent document 3: JP 56/41828A (1981)
Patent document 4: JP 55/47224A (1980)
Patent document 5: JP 48/71392A (1973)
Patent document 6: JP 48/71392A (1973)
Patent document 7: JP 50/158595A (1975)
Patent document 8: Japanese Patent 3838281
Patent document 9: Japanese Patent 3583170
Patent document 10: Japanese Patent 3170234
Patent document 11: JP 2001/26420A
Patent document 12: JP 2000/34121A
Patent document 13: JP 2004/323332A
Patent document 14: JP 11/116,239A (1999)
Patent document 15: JP 10/287,421A (1998)
Patent document 16: JP 2006/335578A

DISCLOSURE OF INVENTION

Problems to be Solved by the Invention

Thus, there has been a growing demand for powder cosmetics in which the powder components do not aggregate and the surface powder component causes no caking in a pressed product, despite a large amount of oily component comprised therein. The purpose of the present invention is to provide such a powder cosmetic.

Another purpose of the present invention is to provide a technique for producing platy calcium sulfate dihydrate for use in the above powder cosmetics in a milder and safer condition and at lower cost than in the past.

Means for Solving the Problems

In order to solve the above problems, the present inventors worked to search a powder component which allows powder cosmetics to contain a larger amount of oily component from a wide variety of organic and inorganic compounds. As a result, the inventors found that the blending of calcium sulfate dihydrate as a powder component into the cosmetics led to the solution of the above problems. The inventors further worked to study a much better process for producing chemical gypsum than the conventional processes, and found that when a calcium salt such as hydrated lime is dissolved in an organic acid such as acetic acid and then allowed to react with an aqueous solution of sulfuric acid at around room temperature, platy calcium sulfate dihydrate is precipitated in a safer condition. Thus, the present invention was completed.

The present invention was completed based on the above findings. The first invention provides a powder cosmetic comprising calcium sulfate dihydrate and an oily component.

The second invention provides a process for producing platy calcium sulfate dihydrate which comprises dissolving a calcium salt in an organic acid, and reacting the resulting calcium solution with sulfuric acid.

Effect of the Invention

The present invention provides excellent powder cosmetics, in which no aggregation of powder occurs, the character of dry touch of the powder itself is kept, and no caking occurs in a pressed product, even when a large amount of oily component is blended.

Thus, the powder cosmetics of the present invention can favorably be used in a form of such powder cosmetics as powder foundation, eye shadow, face powder, and the like.

According to the process for production of the present invention, the platy calcium sulfate dihydrate for use in the above powder cosmetics can be produced in a mild reaction condition at around room temperature by utilizing an organic acid. In addition, the organic acid used in this process can be recovered and recycled; thus, an economically beneficial and environmentally friendly process is provided.

BEST MODE FOR CARRYING OUT THE INVENTION

The powder cosmetics of the present invention may be produced in the same way as the conventional powder cosmetics, except that a part or the whole of the powder component used in the conventional powder cosmetics is replaced with calcium sulfate dihydrate.

In the powder cosmetics of the present invention, the calcium sulfate dihydrate (gypsum) used as a part or the whole of the powder component is not particularly limited, as far as it does not undermine the effect of the invention; thus, conventionally available food additives, those with the grade used as reagents and the like, may be employed. The calcium sulfate dihydrate is partially in a form of plates, with which the powder cosmetic can contain a larger amount of oily component than in the case of using the conventional extender. Further, the calcium sulfate salt may be in a form of anhydrous salt (hard gypsum) and half hydrate (calcined gypsum) in addition to the dihydrate, but the anhydrous salt and the half hydrate cannot be utilized practically since they are inferior to the dihydrate in extensiveness on the skin, touch, and amount of the oily component to be absorbed.

In the powder cosmetics of the present invention, it is preferable to use platy calcium sulfate dihydrate as the above-mentioned calcium sulfate dihydrate. This is in a form of plates, $1/10$ or less the thickness of a typical calcium sulfate dihydrate, and excellent in texture. The platy calcium sulfate dihydrate specifically means the crystals of calcium sulfate dihydrate with 20-200 μm, preferably 20-150 μm in major axis; 10-100 μm, preferably 10-50 μm in minor axis; 0.5-3 μm, preferably 0.5-2 μm in thickness; and the ratio of the major axis to the minor axis being 1-10, preferably 1-5; and the ratio of the major axis to the thickness (aspect ratio) being 10-400, preferably 10-100.

Such platy calcium sulfate dihydrate can be produced according to the conventional ways, for example, the process as described in Kameyama et al., "Synthesis of platy calcium sulfate from calcium carbonate and sulfuric acid", the Report of Industrial Technology Center of Okayama Prefecture, No. 16 (1989); JP 2006/335578A; or the process developed by the present inventors as described below.

An example of the process for producing the above platy calcium sulfate dihydrate is as follows. In the first step, calcium carbonate (10 g) is suspended into water (1 L) to give a calcium carbonate suspension. Next, 0.1M sulfuric acid (1 L) is dropwise added to this suspension at a rate of about 100 mL per minute, and the resulting precipitate is collected by filtration to yield platy calcium sulfate dihydrate. The resulting platy calcium sulfate dihydrate may be dried at about 80° C. to remove water except the crystal water.

Also, the process developed by the present inventors for producing the platy calcium sulfate dihydrate is carried out as follows. A calcium salt is dissolved in an organic acid to give a calcium solution, which is then allowed to react with sulfuric acid to yield the platy calcium sulfate dihydrate as precipitate.

The calcium salt for use in the above production process preferably includes, but is not limited to, hydrated lime, quicklime, calcium carbonate, and so on, in view of economical reasons; in particular, hydrated lime is preferred. In this connection, as for the above calcium salts, it is preferable to use those in which the heavy metal content is low.

The organic acid for use in the above production process preferably includes, but is not limited to, acetic acid, formic acid, lactic acid, propionic acid, and tartaric acid; and acetic acid is particularly preferred. These organic acids may be diluted with pure water to about 90 mass % (hereinafter, simply referred to as "%") in advance.

The condition for dissolving the above calcium salt in the organic acid is not particularly limited; for example, the calcium salt is suspended in pure water, to which the organic acid is added and stirred to dissolve the calcium salt. The calcium salt suspended in pure water may preferably be used in the amount so that the calcium concentration is 0.05-1.0 mol/L in the calcium solution. The organic acid such as acetic acid to be added may preferably be used in an amount of 1 to 3 equivalents, particularly 2 equivalents, to the calcium salt added to pure water.

Next, the calcium solution prepared in the above step is allowed to react with sulfuric acid. The condition for the reaction of the calcium solution with sulfuric acid is not particularly limited; for example, sulfuric acid may be added to the calcium solution with stirring. The concentration of sulfuric acid to be added is not particularly limited, and the total amount of sulfuric acid to be added is preferably 1 to 1.5 equivalents, particularly 1 equivalent, to the calcium salt. The way of addition of sulfuric acid is not particularly limited; preferably, sulfuric acid may be added slowly, e.g. dropwise, to the calcium solution. The rate of addition is, though not particularly limited, preferably 0.2 L to 4.0 L per minute. Further, the reaction of the above calcium solution with sulfuric acid may be carried out at a temperature of 5° C. to 70° C., preferably 15° C. to 25° C., though not particularly limited. Further, the sulfuric acid to be added may be diluted with pure water to about 75% in advance.

After termination of the reaction, the platy calcium sulfate dihydrate precipitates. The precipitated platy calcium sulfate dihydrate may be recovered by means of separation such as filtration, filter press, centrifugation, and so on. Also, after precipitation of the platy calcium sulfate dihydrate, an alkaline material such as sodium hydroxide may be added thereto to neutralize an excess of the acid, and thereafter pure water may further be added to dilute an excess of neutralized product (salts).

The above-prepared platy calcium sulfate dihydrate, if required, may be dried. The drying cannot be carried out at a temperature of 100° C. or higher considering the character of the calcium sulfate dihydrate. The drying at 100° C. or higher will cause dehydration from the dihydrate to yield the ½ hydrate. Therefore, the drying is preferably carried out at a temperature of 80° C. or lower for a long period of time, at least 12 hours. Further, the platy calcium sulfate dihydrate after drying, if required, may be properly pulverized.

The above-mentioned platy calcium sulfate dihydrate is in the form of thinner plates and has excellent characteristic properties in transparency, soft touch, extensiveness, inherent gloss, and so on in comparison with the known extender such as talc or sericite. Since the platy calcium sulfate dihydrate contains 20% of water in the form of crystal water and the like, no hard aggregate is formed as in talc in mixing with the oily component, keeping the characteristic properties such as dry touch of the powder even in using a large amount of the oily component. Thus, the platy calcium sulfate dihydrate is a very useful material as an extender for cosmetics, particularly for powder foundation and the like.

The content of the calcium sulfate dihydrate to be blended into the powder cosmetics of the invention is 10 to 90%, preferably 15 to 70% as the dihydrate.

On the other hand, the oily component for use in the powder cosmetics of the present invention includes those being liquid at room temperature, for example, hydrocarbon such as liquid paraffin, silicone oil such as KF99-1 (Shin-Etsu Chemical Co., Ltd.), ester oils such as octyldodecyl oleate (OOD; Shin-ei Chemical Co., Ltd.), fats and oils, higher fatty acids, higher alcohols; vaseline (paste state at room temperature); and cetanol (solid at room temperature). These oily components may be used in combination. Particularly, in the powder cosmetics of the present invention, the oily component being liquid at room temperature is preferably used in combination with paste-state one and/or solid one, because the resulting powder cosmetic can tighten slightly firm and the powder scraped off from the surface with a sponge becomes relatively small, thereby attaining the greater usability of the cosmetic. The content of the oily component to be blended in the powder cosmetics of the invention is 5-40%, preferably 5-35%.

In the powder cosmetics of the present invention, when calcium sulfate dihydrate, particularly platy calcium sulfate dihydrate, is used as a part or the whole of the powder component, a larger amount of oily component can be blended than in the conventional powder cosmetics. In the context of the present application, the powder cosmetic comprising 15% to 40% oily component, preferably 15-35%, is referred to as "oil-rich cosmetic".

In addition to the above-mentioned essential components, the powder cosmetics of the present invention may contain the following components used in the conventional cosmetics, as long as they do not hinder the effect of the invention: powder components including inorganic powder such as mica, talc, and sericite, organic powder or surface-processed products thereof such as silk powder, white pigments such as titanium dioxide, coloring pigments such as iron oxide red, and glossy pigments such as mica titanium; surface-activating component; moisturizing component; UV absorbing component; antiseptic component; beauty component; fragrance, and the like.

The powder cosmetics of the present invention may be produced in the same way as the conventional cosmetics, except that the calcium sulfate dihydrate and the oily component are used as essential components. Specifically, in the process for producing the cosmetics containing the conventional powder component and oily component, calcium sulfate dihydrate may be used in place of a part or the whole of the conventional powder.

When a large amount of the oily component is blended into the powder cosmetics of the present invention, for example, the process as described in JP 7/55892B (1995), wherein the oily component is added to the cosmetic after molding to increase the content of the oily component, or the method as developed by the present inventors, wherein spherical powder is added to the powder cosmetic to increase the content of the oily component, may be employed.

Among the processes for blending a large amount of oily component into the powder cosmetics, the process for increasing the content of oily component by adding the oily component to the cosmetic after molding may be carried out by first press-molding the powder cosmetic containing 5-20% oily component in a metallic mold, and then dropping or spraying the desired amount of oily component on the surface of the powder cosmetic without damaging the surface so that the oily component is absorbed into the powder cosmetic.

The process for increasing the content of oily component by adding the spherical powder into the powder cosmetic may be carried out simply by adding the spherical powder into the powder cosmetic.

The above-mentioned spherical powder includes, for example, powders derived from inorganic materials such as silica or polymers such as silicone rubber and silicone resin, or their surface-processed products, which have a spherical form, preferably exactly spherical form, with the average particle size of about 1-15 μm. In the present invention, above all, hydrophobic spherical powder may preferably be used, since its fluidity is kept after mixing with the oily component, allowing the continuous production of the powder cosmetics. Such hydrophobic spherical powder includes silicone complex powder prepared by coating silicone rubber with silicone resin, e.g., KSP100 (average particle size 5 μm), KSP101 (average particle size 12 μm), KSP105 (average particle size 2 μm) (all are the products of Shin-Etsu Chemical Co., Ltd.) and the like. The amount of the spherical powder is 1-15%, preferably 5-10% in the powder cosmetics, though it is not particularly limited.

Thus resulting powder cosmetics of the present invention are capable of comprising a large amount of oily component as compare with the conventional cosmetics, and accordingly, another oily component which is particularly beneficial for the skin, such as squalane, may be contained besides the basic material oily component. Furthermore, even though the same amount of the oily component as that of the conventional powder cosmetics is blended, the resulting powder cosmetic can give dry touch with less oiliness.

The cosmetics which readily exhibit the effect of the powder cosmetics of the present invention include those containing a powder component and an oily component, for example, powder foundation, eye shadow, cheek color, face powder, and so on; above all, press-packed cosmetics are preferred, and particularly powder foundation and eye shadow are preferred. When the powder cosmetics of the present invention are formulated into powder foundation and eye shadow, it is possible to obtain the products which is not dusty, and is excellent in moisturizing feeling and adhesion to the skin, resulting in a long lasting make-up naturally adapted to the skin without unevenness, kink, somber color, nor coming-off.

EXAMPLES

The present invention will be explained by the following Examples which are not intended as a limitation thereof.

Reference Example 1

Figure 1:
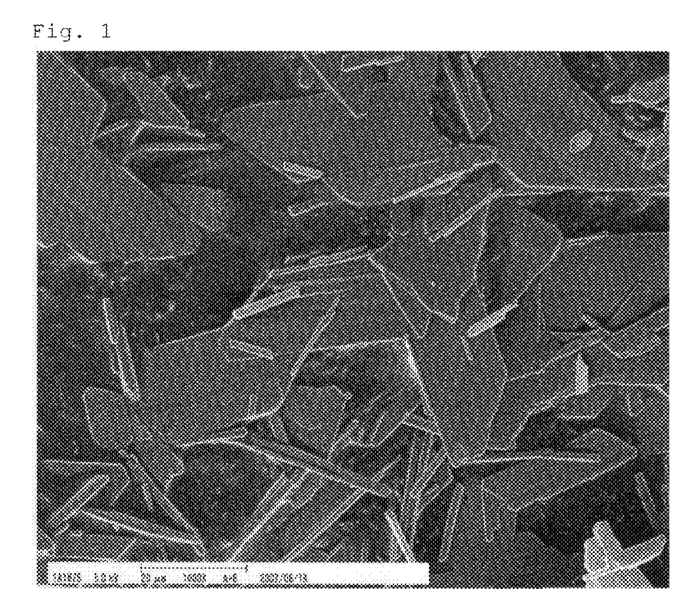
FIG. 1 shows an electron microphotograph (1000 magnifications) of the platy calcium sulfate dihydrate produced in Reference Example 1.

Preparation of Platy Calcium Sulfate Dihydrate:

Calcium carbonate (10 g) was suspended into 1 L of water at room temperature to give a suspension of calcium carbonate. Then, 1 L of 0.1M sulfuric acid was dropwise added to the suspension at a rate of about 100 mL/minute, and the resulting precipitate was collected by filtration to give calcium sulfate. This was then dried at 80° C. so that no water except the crystal water was contained. The calcium sulfate was obtained as the dihydrate in the form of plates (flake), with 20-150 μm in major axis, 10-50 μm in minor axis, 0.5-2 μm in thickness, the ratio of the major axis to the minor axis being 1-10, and the ratio of the major axis to the thickness (aspect ratio) being about 10-100. FIG. 1 shows an electron microphotograph of the platy calcium sulfate dihydrate.

It is generally known that calcium sulfate dihydrate loses the water by heating at 150° C. or higher to turn into the anhydrous salt. Based on this fact, the water content of the above-prepared platy calcium sulfate was compared with that of a commercially available calcium sulfate dihydrate (super high grade reagent) which had been dried in the same condition. The drying was conducted at 400° C. for 2 hours.

TABLE 1

| Sample | Before Treat (g) | After Treat (g) | Water (g) | Coefficient of Crystal Water |
|---|---|---|---|---|
| Platy calcium sulfate dihydrate | 1.0310 | 0.8153 | 0.2157 | 2.00 |
|  | 1.0732 | 0.8503 | 0.2229 | 1.98 |
| Calcium sulfate dihydrate (Super high grade) | 1.0578 | 0.8361 | 0.2217 | 2.00 |
|  | 0.9695 | 0.7664 | 0.2031 | 2.00 |

From the above results, the resulting platy calcium sulfate was confirmed exactly to be the dihydrate.

Test 1

Comparison of the Characteristic Properties of Calcium Sulfate Dihydrate Powders:

The characteristic properties of the platy calcium sulfate dihydrate used in the present invention were compared with those of the general extender. The powder component was homogeneously mixed with the oily component at the rate as shown in Table 2, and pressed on a metal plate. The state of the surface of the pressed product was voluntarily evaluated visually, and further, the ease of removal with a sponge was evaluated according to the following evaluation standard. These results are shown in Table 2.

<Evaluation Standard for the Ease of Removal with a Sponge>

(Evaluation)(Content)

○: No caking occurs after repeated removal with a sponge

X: Caking occurs after rubbing 3-4 times with a sponge and cannot be removed.

<Results>

When the platy calcium sulfate dihydrate and the oily component were used, the surface of the product was kept in a powdery state even in blending of 20% oily component and removed well with a sponge (Product 2).

On the other hand, when talc or sericite was used together with the oily component, the appearance of each product looked like a glassy hard stone in blending of 20% oily component, and the surface could not be removed at all with a sponge (Comparative products 1 and 2).

Further, when the platy calcium sulfate dihydrate and the oily component were used, the surface of the product was kept in a rough or powdery state even in blending of 5% or more oily component and removed well with a sponge (Products 3 and 4).

On the other hand, when talc was used with the oily component, there was no problem in the state of the surface and the removal with a sponge in the presence of 5% oily component, but when 7% oily component was blended, the surface became glassy and hard, and could not be removed at all with a sponge (Comparative products 3 and 4).

Thus, when the platy calcium sulfate dihydrate was used, there occurred no deterioration in the state of the surface and the removal with a sponge in a wide range of the amount of oily component to be added. These excellent products could be utilized as face powder.

Example 1

Preparation of Powder Foundation (1):

As shown in Table 3, powder foundations were prepared according to the following production process. These powder foundations were evaluated for the surface state and the ease of removal with a sponge according to the same evaluation standard as in Test 1. The results are shown in Table 3.

TABLE 2

| Component (%) | Product 1 | Product 2 | Comparative product 1 | Comparative product 2 | Product 3 | Comparative product 3 | Product 4 | Comparative product 4 |
|---|---|---|---|---|---|---|---|---|
| Platy calcium sulfate dihydrate [1] | 82 | 80 | — | — | 95 | — | 93 | — |
| Talc | — | — | 80 | — | — | 95 | — | 93 |
| Sericite | — | — | — | 80 | — | — | — | — |
| Squalane | 18 | 20 | 20 | 20 | 5 | 5 | 7 | 7 |
| State of surface | Powdery | Powdery | Glassy Hard | Glassy Hard | Rough | Powdery | Powdery | Firm |
| Ease of removal with a sponge | ○ | ○ | X | X | ○ | ○ | ○ | X |

[1] Prepared in Reference Example 1

TABLE 3

| Component (%) | Product 5 | Product 6 | Comparative product 5 | Product 7 | Product 8 | Comparative product 6 | Comparative product 7 | Comparative product 8 | Comparative product 9 |
|---|---|---|---|---|---|---|---|---|---|
| 1 Calcium sulfate dihydrate[1] | 51 | — | — | — | — | — | — | — | — |
| 2 Platy calcium sulfate dihydrate[2] | — | 51 | — | 10 | 30 | — | — | — | — |
| 3 Talc | — | — | 51 | 50 | 27 | 63 | 61 | — | — |
| 4 Sericite | — | — | — | — | — | — | — | 60 | 59 |
| 5 Titanium dioxide | 10 | 10 | 10 | 10 | 10 | 10 | 10 | 10 | 10 |
| 6 Mica | 15 | 15 | 15 | 15 | 15 | 15 | 15 | 15 | 15 |
| 7 Yellow iron oxide | 1.5 | 1.5 | 1.5 | 1.5 | 1.5 | 1.5 | 1.5 | 1.5 | 1.5 |
| 8 Red iron oxide | 0.4 | 0.4 | 0.4 | 0.4 | 0.4 | 0.4 | 0.4 | 0.4 | 0.4 |
| 9 Iron black | 0.1 | 0.1 | 0.1 | 0.1 | 0.1 | 0.1 | 0.1 | 0.1 | 0.1 |
| 10 Ester oil[3] | 11 | 11 | 11 | 6.5 | 8 | 5 | 6 | 6.5 | 7 |
| 11 Silicone oil[4] | 11 | 11 | 11 | 6.5 | 8 | 5 | 6 | 6.5 | 7 |
| State of Surface | Powdery | Powdery | Glassy Hard | Powdery | Powdery | Powdery | Hard | Powdery | Hard |
| Ease of removal with a sponge | ○ | ○ | X | ○ | ○ | ○ | X | ○ | X |

[1]Commercially available calcium sulfate dihydrate (super high grade)
[2]Prepared in Reference Example 1
[3]OOD (Shin-ei Chemical Co., Ltd.)
[4]KF99-1 (Shin-Etsu Chemical Co., Ltd.)

<Production Process>

A: Components (1) to (9) are mixed and dispersed homogeneously.

B: Components (10) and (11) are mixed homogeneously at room temperature.

C: B is dispersed into the A components.

D: C was press-packed in a metallic mold to give powder foundation.

<Results>

Powder foundation prepared from calcium sulfate dihydrate or the platy calcium sulfate dihydrate with the oily components had the surface of a powdery state, which was removed with a sponge without occurring caking at all (Products 5 and 6). On the other hand, the powder foundation prepared by using talc and the oily components in the same rate formed the glassy hard surface, which could not be removed with a sponge at all (Comparative product 5).

In the powder foundation containing the platy calcium sulfate dihydrate, there is no problem even in the content of oily component being 13-22% (Products 6-8). On the other hand, as for the powder foundation containing talc, there was no problem in the content of oily components being 10% (Comparative product 6), but caking occurred when the content of oily components was 12% (Comparative product 7).

Further, in the powder foundation containing sericite, there was no problem in the content of oily components being 13% (Comparative product 8), but caking occurred when the content of oily components was 14% (Comparative product 9).

In this connection, the combined use of talc and platy calcium sulfate dihydrate allowed to increase the content of oily components in comparison with the use of talc alone (Products 7 and 8).

Example 2

Preparation of Powder Foundation (2):

As shown in Table 4, a powder foundation was prepared according to the following production process. The powder foundation was evaluated for the surface state and the ease of removal with a sponge according to the same evaluation standard as in Test 1. The results are shown in Table 4.

TABLE 4

| Component (part by wt) | Product 9 |
|---|---|
| 1 Platy calcium sulfate dihydrate[1] | 53 |
| 2 Titanium dioxide | 10 |
| 3 Mica | 15 |
| 4 Yellow iron oxide | 1.5 |
| 5 Red iron oxide | 0.4 |
| 6 Iron black | 0.1 |
| 7 Liquid paraffin* | 3.0 |
| 8 Ester oil[2]* | 3.0 |
| 9 Silicone oil[3]* | 5.0 |
| 10 Squalane* | 3.0 |
| 11 Vaseline** | 3.0 |
| 12 Cetanol*** | 3.0 |
| State of Surface | Powdery |
| Ease of removal with a sponge | ○ |

[1]Prepared in Reference Example 1
[2]OOD (Shin-ei Chemical Co., Ltd.)
[3]KF99-1 (Shin-Etsu Chemical Co., Ltd.)
*Liquid at room temperature
**Paste at room temperature
***Solid at room temperature <Production Process>

A: Components (1) to (6) are mixed and dispersed homogeneously.

B: Components (7) to (12) are mixed homogeneously at room temperature.

C: B is dispersed into the A components.

D: C was press-packed in a metallic mold to give powder foundation.

<Result>

The powder foundation prepared above, though the oily components being paste or solid at room temperature were used in addition to the liquid oily component at room temperature, had a surface state comparable to those prepared only with an oily component which is liquid at room temperature. This powder foundation per se tightens slightly firm, from which a relatively small amount of powder is separated by scraping with a sponge, giving an excellent usability.

Example 3

Preparation of Powder Foundation (3):
(1) Preparation of Powder Foundation

As shown in Table 5, a powder foundation was prepared according to the following production process. The powder foundation was evaluated for the surface state and the ease of removal with a sponge according to the same evaluation standard as in Test 1. The results are shown in Table 5.

TABLE 5

| Component (part by wt) | Product 10 |
|---|---|
| 1 Platy calcium sulfate dihydrate[1] | 33 |
| 2 Titanium dioxide | 10 |
| 3 Mica | 15 |
| 4 Yellow iron oxide | 1.5 |
| 5 Red iron oxide | 0.4 |
| 6 Iron black | 0.1 |
| 7 Ester oil[2] | 10 |
| 8 Silicone oil[3] | 10 |
| State of Surface | Powdery |
| Ease of removal with a sponge | ◯ |

[1]Prepared in Reference Example 1
[2]OOD (Shin-ei Chemical Co., Ltd.)
[3]KF99-1 (Shin-Etsu Chemical Co., Ltd.)

<Production Process>
A: Components (1) to (6) are mixed and dispersed homogeneously.
B: Components (7) and (8) are mixed homogeneously at room temperature.
C: B is dispersed into the A components.
D: C was press-packed in a metallic mold to give powder foundation (8 g).
<Result>

For the powder foundation prepared above, the surface was kept in a state of powder, and there was no problem in the removal with a sponge at all.

(2) Preparation of the Powder Foundation in which the Content of the Oily Components is Increased In the powder foundation (8 g) prepared in the above section (1), the content of oily components was increased from 25% to 40% to give a powder foundation (Product 11) according to the following process as described in JP 7/55892B (1995).

<Process for Increasing the Content of Oily Components>
E: Onto the powder foundation were added 2 g of oily components (a mixture of the components (7) and (8)) without damaging the surface of the powder foundation so that it was absorbed into the powder.
<Result>

There was no change in the state of the surface of the above-prepared powder foundation in which the content of oily components was increased as compared with that before addition of the oily components, and no oozing-out of the oily components was observed. In addition, there was no problem in the removal with a sponge, and there occurred no caking on the surface.

In the powder foundation prepared according to the process as described in JP 7/55892B (1995), it was necessary to make holes on the metallic plate in order to let off the excess oily component that the powder was unable to absorb. On the other hand, the powder foundation of the present invention requires no hole on the metallic plate, since it has a high absorbability for the oily component owing to the use of the platy calcium sulfate dihydrate.

Example 4

Preparation of Powder Foundation:

As shown in Table 6, powder foundations were prepared according to the following production process. In the course of the production process, the fluidity and the press forming ability of the powder after mixing and dispersing were evaluated according to the following standard. FIG. 6 shows the results.

<Production Process>
A: Components (1) to (9) are mixed and dispersed homogeneously.
B: Components (10) and (11) are mixed homogeneously at room temperature.
C: B is dispersed into the A components.
D: C was press-packed in a metallic mold to give powder foundation.

TABLE 6

| | Component (%) | Product 12 | Product 13 | Product 14 | Product 15 | Product 16 |
|---|---|---|---|---|---|---|
| 1 | Platy calcium sulfate dihydrate[1] | 30 | 30 | 30 | 30 | 30 |
| 2 | Titanium dioxide | 10 | 10 | 10 | 10 | 10 |
| 3 | Mica | 15 | 15 | 15 | 15 | 15 |
| 4 | Yellow iron oxide | 1 | 1 | 1 | 1 | 1 |
| 5 | Red iron oxide | 0.4 | 0.4 | 0.4 | 0.4 | 0.4 |
| 6 | Iron black | 0.1 | 0.1 | 0.1 | 0.1 | 0.1 |
| 7 | Talc | 23.5 | 18.5 | 18.5 | — | — |
| 8 | Silicone complex powder[2] | — | — | 10 | 13.5 | — |
| 9 | Inorganic silica spherical beads[3] | — | — | — | — | 13.5 |
| 10 | Ester oil[4] | 10 | 12.5 | 12.5 | 15 | 15 |
| 11 | Silicone oil[5] | 10 | 12.5 | 12.5 | 15 | 15 |
| Maintenance of fluidity and press forming ability of powder after mixing and stirring | | ◯ | Δ | ◯ | ◯ | Δ |

[1]Prepared in Reference Example 1
[2]KSP-100 (Shin-Etsu Chemical Co., Ltd.)
[3]God Ball E-16C (Suzuki Yushi Industrial Co., Ltd.)
[4]OOD (Shin-ei Chemical Co., Ltd.)
[5]KF99-1 (Shin-Etsu Silicones)

<Evaluation Standard for the Maintenance of Fluidity and the Press Forming Ability of the Powder after Mixing and Stirring>

(Evaluation)(Content)

◯: The powder after dispersion kept the fluidity allowing the continuous press packing in a metallic mold Δ: The powder after dispersion lost the fluidity, but it could be press-packed in a metallic mold.

X: No fluidity was observed in the powder after dispersion, and it could not be press-packed in a metallic mold.

<Result>

In the powder foundation prepared from the platy calcium sulfate dihydrate and the oily components, a mixture of the powder and the oily components did not lose the fluidity after mixing and stirring even in the presence of 20% oily components, and it could be press-packed on a metallic mold continuously (Product 12).

When the content of oily components was 25%, the stirred powder granulated to form huge lumps resulting in lost fluidity, but it could be batch-press-packed in a metallic mold (Product 13). Even though the platy calcium sulfate dihydrate was added to the powder cosmetic, the addition of the oily components over this level would make it difficult to press-pack in a metallic mold.

When hydrophobic spherical powder was added to the components of the powder cosmetic in order to make it possible to press-pack in a metallic mold, the mixture did not lose the fluidity after stirring and it could be press-packed continuously in a metallic mold even in the presence of 25% and 30% of oily components (Product 14 and Product 15). Further, when the content of oily components was 30%, batch-press-pack could be achieved even though non-hydrophobic spherical powder was added (Product 16).

Example 5

Preparation of Eye Shadow:

As shown in Table 7, eye shadows were prepared according to the following production process. These eye shadows were evaluated for the ease of removal with a sponge according to the same evaluation standard as in Test 1. The results are shown in Table 7.

TABLE 7

| | Component (%) | Product 17 | Product 18 | Comparative product 10 | Comparative product 11 |
|---|---|---|---|---|---|
| 1 | Platy calcium sulfate dihydrate[1) | 38.0 | 33.0 | — | — |
| 2 | Mica | 20.0 | 20.0 | 20.0 | 20.0 |
| 3 | Talc | — | — | 47.0 | 43.0 |
| 4 | Yellow ion oxide | 4.0 | 4.0 | 4.0 | 4.0 |
| 5 | Ultramarine | 3.0 | 3.0 | 3.0 | 3.0 |
| 6 | Pearl pigment[2) | 10.0 | 10.0 | 10.0 | 10.0 |
| 7 | Ester oil[3) | 13.0 | 15.0 | 8.0 | 10.0 |
| 8 | Silicone oil[4) | 12.0 | 15.0 | 8.0 | 10.0 |
| Ease of removal with a sponge | | ◯ | ◯ | ◯ | X |

[1)Prepared in Reference Example 1
[2)Prominence SF (Ninon Koken Kogyo Co., Ltd.)
[3)OOD (Shin-Ei Chemical Co., Ltd.)
[4)KF99-1 (Shin-Etsu Silicones)

<Production Process>

A: Components (1) to (6) are mixed and dispersed homogeneously.

B: Components (7) and (8) are mixed homogeneously at room temperature.

C: B is mixed and dispersed into the A components.

D: C was press-packed in a metallic mold to give eye shadow.

<Result>

In the eye shadow prepared from the platy calcium sulfate dihydrate and the oily components, there was no problem in the removal with a sponge in the presence of 20% and 30% of oily components (Products 17 and 18).

On the other hand, in the eye shadow prepared using mica and talc together with the oily components, there was no problem in the removal with a sponge in 16% oily components (Comparative product 10), but a problem occurred in the removal with a sponge at 20% (Comparative product 11).

Example 6

Production of Platy Calcium Sulfate Dihydrate (1):

In a 100 L volume tank was placed 72 L of pure water. Then, hydrated lime (933 g) was added thereto with stirring to give a homogeneous suspension of calcium. The concentration of the calcium salt in the suspension was 0.175 mol/L. To this suspension was added 1680 g of 90% acetic acid solution and dissolved to give a clear solution (hereinafter referred to as "mother liquor for reaction"). On the other hand, 1647 g of 75% sulfuric acid was dissolved in 18 L of pure water, to which was slowly added the mother liquor for reaction with stirring. After termination of the addition, the stirring was stopped, and the resulting crystals were allowed to precipitate. After enough precipitation, the supernatant was eliminated. Sodium hydroxide was added to the mother liquor for reaction containing the precipitate to neutralize acetic acid generated by the reaction. Thereafter, the tank was filled with addition of pure water to dilute the salts generated after neutralization. After washing, the supernatant was eliminated to collect the precipitate, which was further moved to a centrifuge and dehydrated to give a cake. The resulting cake was moved into a drier and dried at 80° C. for 12 hours. After drying, the cake was crushed with a crusher into fine powder. Thus, 1.1 kg of platy calcium sulfate dihydrate was obtained. The pure water of a quality surpassing a definite standard (0.1MΩcm), which was obtained using a pure water generator by means of reverse osmosis, was used in all of Examples.

Figure 2:
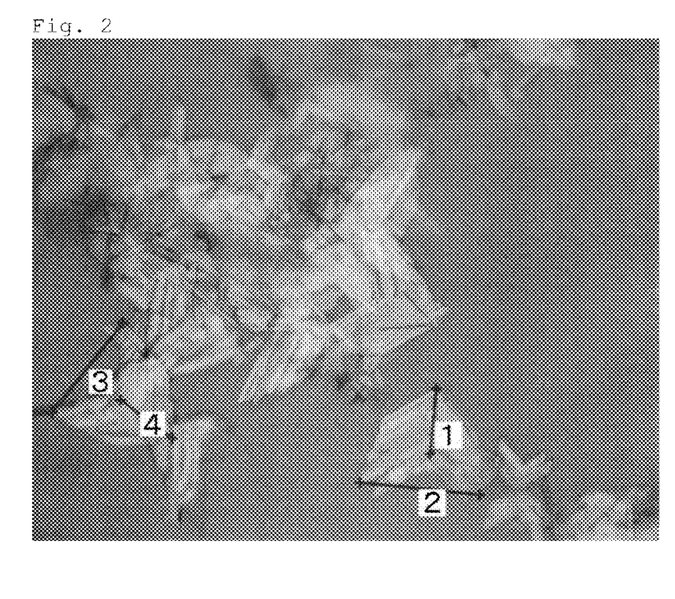
FIG. 2 shows a microphotograph (200 magnifications) of the platy calcium sulfate dihydrate produced in Example 5 (wherein 1 indicates 42 μm, 2: 77 μm, 3: 73 μm, and 4: 41 μm).

The crystals of platy calcium sulfate dihydrate prepared in the above Example was of 20-160 μm in major axis, 10-80 μm in minor axis, and 0.5-2 μm in thickness, with the ratio of the major axis to the minor axis being 1-5, and the ratio of the major axis to the thickness (aspect ratio) being 10-250. FIG. 2 shows a microphotograph of the platy calcium sulfate dihydrate.

Example 7

Production of Platy Calcium Sulfate Dihydrate (2):

In a 10 L volume tank was placed 8 L of pure water. Then, hydrated lime (370 g) was added thereto with stirring to give a homogeneous suspension of calcium. The concentration of the calcium salt in the suspension was 0.625 mol/L. To this suspension was added 666 g of 90% acetic acid solution and dissolved to give a clear solution as mother liquor for reaction. On the other hand, 653 g of 75% sulfuric acid was dissolved in 2 L of pure water, to which was slowly added the mother liquor for reaction with stirring. After termination of the addition, the stirring was stopped, and the resulting crystals were allowed to precipitate. After enough precipitation, the supernatant was eliminated. Sodium hydroxide was added to the mother liquor for reaction containing the precipitate to neutralize acetic acid generated by the reaction. Thereafter, the tank was filled with addition of pure water to dilute the salts generated after neutralization. After washing, the supernatant was eliminated to collect the precipitate, which was further moved to a centrifuge and dehydrated to give a cake. The resulting cake was moved into a drier and dried at 80° C. for 12 hours. After drying, the cake was crushed with a crusher into fine powder. Thus, 0.7 kg of platy calcium sulfate dihydrate was obtained.

The crystals of platy calcium sulfate dihydrate prepared in the above Example was of 20-80 μm in major axis, 10-40 μm in minor axis, and 1-3 μm in thickness, with the ratio of the major axis to the minor axis being 1-5, and the ratio of the major axis to the thickness (aspect ratio) being 10-100.

Example 8

Production of Platy Calcium Sulfate Dihydrate (3):

In a 10 L volume tank was placed 8 L of pure water. Then, hydrated lime (37 g) was added thereto with stirring to give a homogeneous suspension of calcium. The concentration of the calcium salt in the suspension was 0.0625 mol/L. To this suspension was added 66.6 g of 90% acetic acid solution and dissolved to give a clear solution as mother liquor for reaction. On the other hand, 65.3 g of 75% sulfuric acid was dissolved in 2 L of pure water, to which was slowly added the mother liquor for reaction with stirring. After termination of the addition, the stirring was stopped, and the resulting crystals were allowed to precipitate. After enough precipitation, the supernatant was eliminated. Sodium hydroxide was added to the mother liquor for reaction containing the precipitate to neutralize acetic acid generated by the reaction. Thereafter, the tank was filled with addition of pure water to dilute the salts generated after neutralization. After washing, the supernatant was eliminated to collect the precipitate, which was further moved to a centrifuge and dehydrated to give a cake. The resulting cake was moved into a drier and dried at 80° C. for 12 hours. After drying, the cake was crushed with a crusher into fine powder. Thus, 0.07 kg of platy calcium sulfate dihydrate was obtained.

The crystals of platy calcium sulfate dihydrate prepared in the above Example was of 20-200 μm in major axis, 10-100 μm in minor axis, and 0.5-2 μm in thickness, with the ratio of the major axis to the minor axis being 1-5, and the ratio of the major axis to the thickness (aspect ratio) being 10-400.

Example 9

Production of Platy Calcium Sulfate Dihydrate (3):

In a 10 L volume tank was placed 8 L of pure water. Then, hydrated lime (37 g) was added thereto with stirring to give a homogeneous suspension of calcium. The concentration of the calcium salt in the suspension was 0.0625 mol/L. To this suspension was added 100.0 g of 90% lactic acid solution and dissolved to give a clear solution as mother liquor for reaction. On the other hand, 65.3 g of 75% sulfuric acid was dissolved in 2 L of pure water, to which was slowly added the mother liquor for reaction with stirring. After termination of the addition, the stirring was stopped, and the resulting crystals were allowed to precipitate. After enough precipitation, the supernatant was eliminated. Sodium hydroxide was added to the mother liquor for reaction containing the precipitate to neutralize lactic acid generated by the reaction. Thereafter, the tank was filled with addition of pure water to dilute the salts generated after neutralization. After washing, the supernatant was eliminated to collect the precipitate, which was further moved to a centrifuge and dehydrated to give a cake. The resulting cake was moved into a drier and dried at 80° C. for 12 hours. After drying, the cake was crushed with a crusher into fine powder. Thus, 0.07 kg of platy calcium sulfate dihydrate was obtained.

The crystals of platy calcium sulfate dihydrate prepared in the above Example was of 20-160 μm in major axis, 10-80 μm in minor axis, and 0.5-2 μm in thickness, with the ratio of the major axis to the minor axis being 1-5, and the ratio of the major axis to the thickness (aspect ratio) being 10-250.

Test 2

Test for Confirmation of Platy Calcium Sulfate Dihydrate:

It is generally known that calcium sulfate dihydrate loses the water by heating at 150° C. or higher to turn into the anhydrous salt. Based on this fact, the water content of the above-prepared platy calcium sulfate was compared with that of a commercially available calcium sulfate dihydrate (super high grade reagent) which had been dried in the same condition. The drying was conducted at 400° C. for 2 hours.

From the test results, all of the platy calcium sulfate prepared in the above Examples were confirmed to be the dihydrate.

INDUSTRIAL APPLICABILITY

The amount of the oily component which can be added to the conventional powder cosmetics containing talc or sericite as an extender is limited to about 15% at the most, and when it was added over this level, caking occurred to worsen the ease of removal with a sponge, resulting in making it inappropriate practically. On the other hand, the powder cosmetic of the present invention in which calcium sulfate dihydrate, particularly platy calcium sulfate dihydrate, is used as an extender, can contain a large amount of oily component without making a sacrifice of the dry touch of the product.

According to the present invention, it is possible to prepare powder cosmetics in which the content of the oily component is increased up to 15%-40%, depending on the combination of powder.

In addition, according to the process for producing platy calcium sulfate dihydrate of the present invention, it is possible to obtain the platy calcium sulfate dihydrate in a milder and safer condition at lower cost utilizing an organic acid than in the conventional processes. Since the organic acid used in this process can be recovered and recycled, the process of the invention is economical and friendly to environment.

BRIEF DESCRIPTION OF DRAWINGS

FIG. 1.

FIG. 2.

The invention claimed is:
1. A powder cosmetic comprising
    platy calcium sulfate dihydrate and an oily component, the
        platy calcium sulfate dihydrate having a length in a
        major axis thereof of 20-200 μm, a width in a minor axis
        of 10-100 μm, a thickness of 0.5-3 μm, and a ratio of
        major axis-to-thickness of 10-400.
2. The powder cosmetic according to claim 1, containing 5-40 mass % of oily component.
3. The powder cosmetic according to claim 1, containing 10-90 mass % of the platy calcium sulfate dihydrate.

4. The powder cosmetic according to claim 1, further comprising spherical powder.

5. The powder cosmetic according to claim 1, being a powder foundation.

6. The powder cosmetic according to claim 1, being an eye shadow.

7. The powder cosmetic according to claim 1, being face powder.

8. The powder cosmetic according to claim 2, containing 10-90 mass % of the platy calcium sulfate dihydrate.

9. The powder cosmetic according to claim 8, further comprising spherical powder.

10. The powder cosmetic according to claim 2, further comprising spherical powder.

11. The powder cosmetic according to claim 3, further comprising spherical powder.

12. A cosmetic powder which is dry to the touch, comprising
    5-40% of an oily component, 10-90% of platy calcium sulfate dihydrate, and 1-15% of spherical power,
    wherein the spherical powder has an average particle size of about 1-15 μm, and
    wherein the platy calcium sulfate dihydrate has a length in a major axis thereof of 20-200 μm, a width in a minor axis of 10-100 μm, a thickness of 0.5-3 μm, and a ratio of major axis-to-thickness of 10-400.

13. A dry to the touch cosmetic powder according to claim 12,
    wherein the platy calcium sulfate dihydrate has a length of 20-150 μm, a width of 10-50 μm, a thickness of 0.5-2 μm, and a ratio of major axis-to-thickness of 10-100.

* * * * *